United States Patent [19]

Bonati et al.

[11] Patent Number: 5,203,781
[45] Date of Patent: Apr. 20, 1993

[54] LUMBAR ARTHROSCOPIC LASER SHEATH

[75] Inventors: Alfred O. Bonati, New Port Richey; Philip Ware, Spring Hill, both of Fla.

[73] Assignee: Meditron Devices, Inc., Hackensack, N.J.

[21] Appl. No.: 814,185

[22] Filed: Dec. 19, 1991

[51] Int. Cl.⁵ .............................................. A61B 17/36
[52] U.S. Cl. ...................................... 606/15; 606/16; 606/13; 128/4; 128/6
[58] Field of Search ................................. 606/13-16; 128/4, 6, 395, 398

[56] References Cited

U.S. PATENT DOCUMENTS

| | | | |
|---|---|---|---|
| 4,211,229 | 7/1980 | Wurster | 606/14 |
| 4,313,431 | 2/1982 | Frank | 606/16 X |
| 4,597,380 | 7/1986 | Raif et al. | 606/14 X |
| 4,760,840 | 8/1988 | Fournier, Jr. et al. | 606/15 |
| 4,920,961 | 5/1990 | Grossi et al. | 606/14 |
| 4,955,882 | 9/1990 | Hakky | 606/16 X |

Primary Examiner—Stephen C. Pellegrino
Assistant Examiner—Jeffrey A. Schmidt
Attorney, Agent, or Firm—Joseph C. Mason, Jr.; Ronald E. Smith

[57] ABSTRACT

A tool that is retrofit to a conventional arthroscope to add multiple functions. The tool includes a sheath that receives the elongate tube of the arthroscope, and a lock that detachably secures the tool to the arthroscope. A hollow base member is mounted to the sheath, and a first opening formed in the sheath provides fluid communication between the hollow interior of the base member and the sheath. An irrigation control valve is mounted to the base member and supplies irrigation fluid to the site of the surgical procedure through an elongate flexible needle that extends from the irrigation control valve to the distal end of the sheath. A suction control valve has an inlet in communication with a source of negative pressure and vacuums irrigation fluid and surgical debris from the site. A laser tube intersects the sheath at a second opening at an angle and delivers coherent light to the site. Thus, the tool adds a total of three functions to the arthroscope.

3 Claims, 3 Drawing Sheets

LUMBAR ARTHROSCOPIC LASER SHEATH

TECHNICAL FIELD

This invention relates to surgical instruments. More particularly, it relates to an apparatus that is retrofit to an existing surgical tool to increase the number of functions performed by the tool.

BACKGROUND ART

A conventional arthroscope is designed to perform two closely related functions, i.e., to illuminate the site of a surgical procedure and to facilitate viewing of the site by the physician. The site is illuminated with incoherent light carried by optical fibers. An objective lens at the distal end of the scope focuses the light and a rod lens carries the light to the physician's eye.

A separate irrigation tool is used to deliver saline solution to the site of the surgical procedure, and still another separate tool vacuums the irrigation solution and debris floating therewithin. Separate tools are also provided for delivering coherent light thereto, and so on.

Thus, multiple incisions are needed to introduce the various tools to the surgical site, or if a single incision is made, then multiple entries through the incision are needed as different tools are used.

Thus, if a retrofit tool could be developed that would attach to an existing arthroscope and supply it with additional functions, then the surgeon could perform multiple surgical procedures without discarding the standard two function arthroscope.

However, the prior art, when considered as a whole as required by law, neither teaches nor suggests that a retrofit tool should be provided or how such a tool could be provided.

DISCLOSURE OF INVENTION

The present invention is provided in the form of a lumbar arthroscopic laser sheath that is detachably securable to a conventional arthroscope having a rod lens and optical fiber means. The novel sheath adds three functions to the existing arthroscope so that the combined tools perform a total of five functions.

The novel tool includes an elongate tubular sheath that slidingly receives the elongate stainless steel outer casing of a conventional arthroscope. A look means is provided at the proximal end of the sheath that performs the function its name implies, i.e., the lock means detachably secures the conventional instrument to the novel sheath.

The novel tool further includes a hollow base member the hollow interior of which is in fluid communication with the hollow interior of the novel sheath. An irrigation port is mounted in a perimeter of the base member and supplies irrigation fluid from a source thereof external to the novel tool to the site of the surgical procedure. A needle extends from the irrigation port to the distal end of the novel sheath, and said needle abuts an outer perimeter of the sheath along its extent so that it does not substantially impair insertion of the outer casing of the scope into the sheath. A suction port is also provided in the perimeter of the base member and it interconnects the hollow interior of the novel sheath with a source of negative pressure external thereto. Thus, the irrigation fluid is easily vacuumed from the site of the procedure. Both the irrigation port and the suction port are provided with valves so that the physician can control the flow rate of the irrigation fluid to the site and the vacuuming rate.

The novel tool further includes a laser tube that intercepts the novel sheath at a predetermined angle. An opening in the sheath admits laser fiber thereinto; the laser fiber extends to the distal end of the sheath, radially outwardly of the outer casing of the scope, and thus supplies coherent light to the site of the procedure to vaporize tissue or other materials.

Thus it is apparent that the primary object of the present invention is to provide a retrofit tool that is detachably securable to a conventional arthroscope to thereby increase the versatility of the conventional arthroscope.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

BEST MODES FOR CARRYING OUT THE INVENTION

Figure 1:
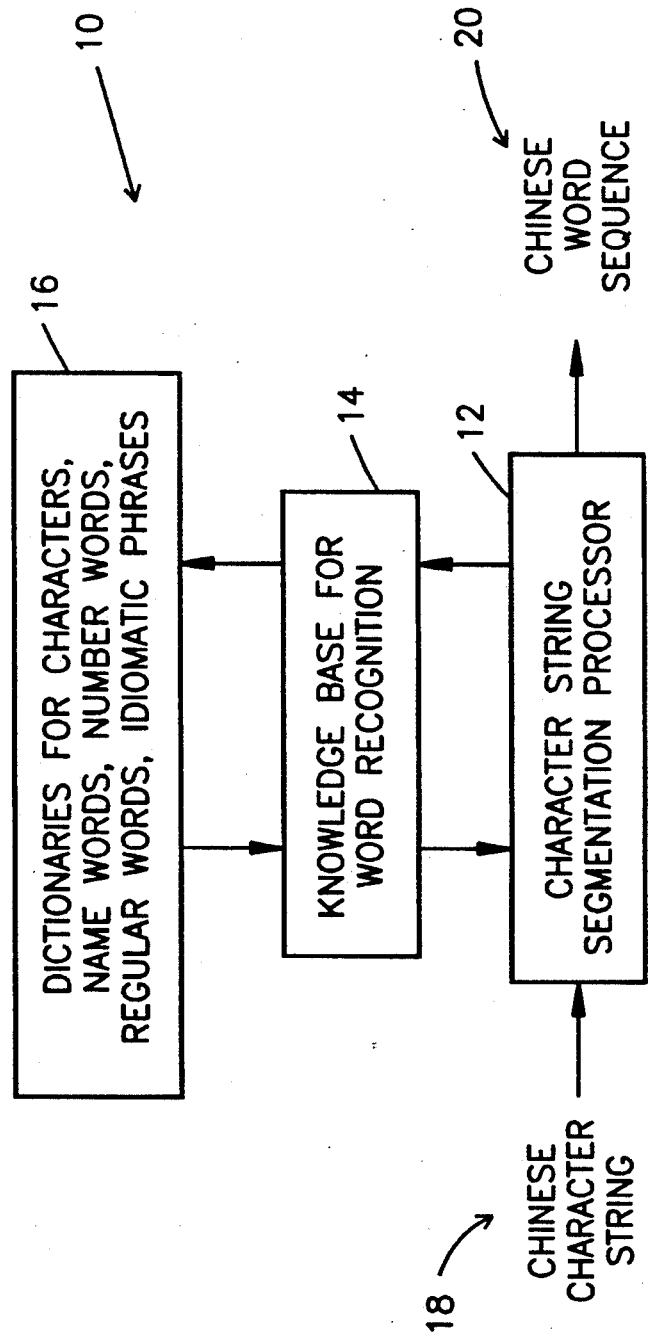
FIG. 1 is a perspective view of the novel tool.
Figure 2:
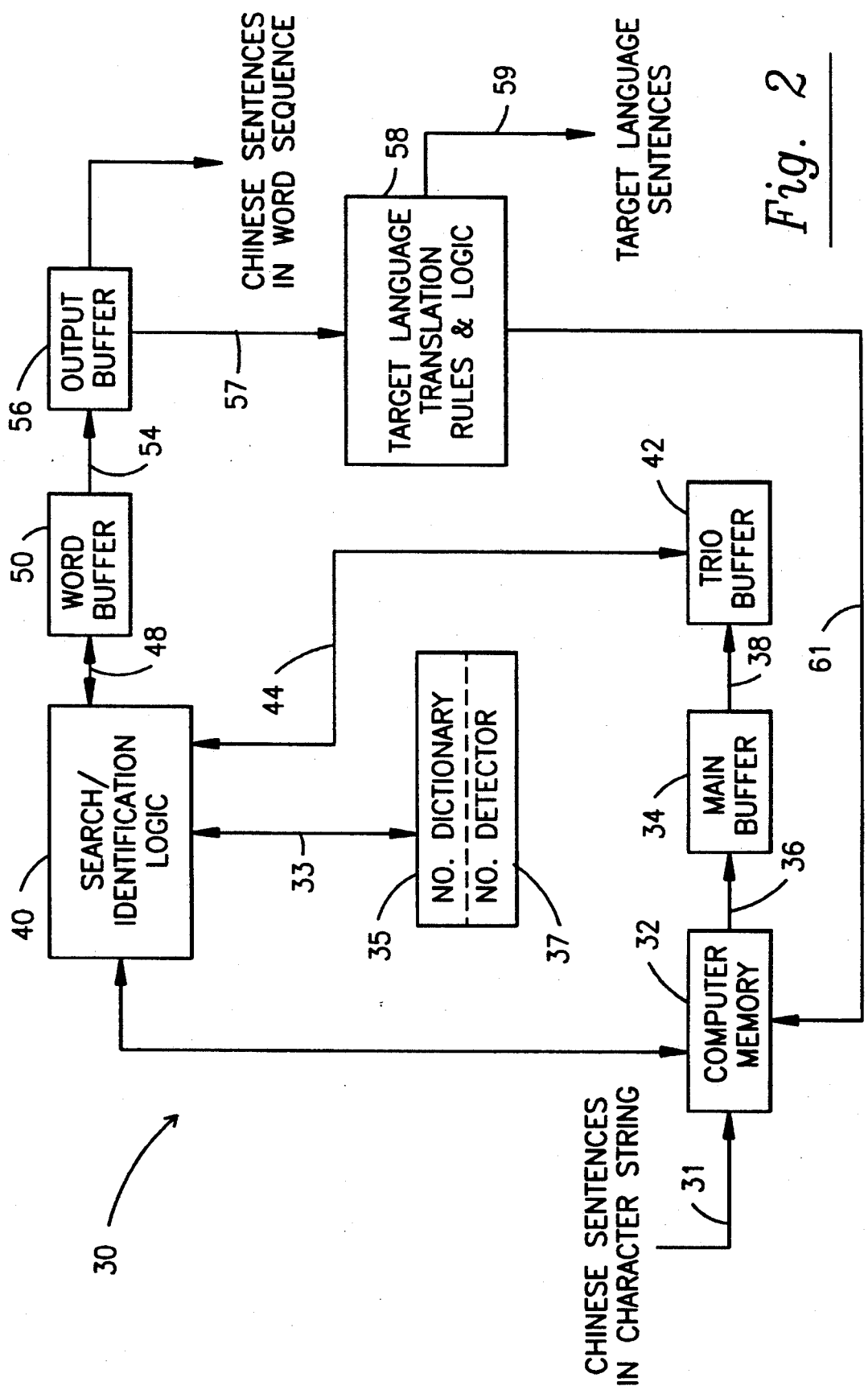
FIG. 2 is a longitudinal sectional view thereof.

Referring now to FIGS. 1 and 2, it will there be seen that the novel lumbar arthroscopic laser sheath is denoted as a whole by the reference numeral 10.

Elongate tube 12 slidingly receives the elongate outer casing 14 (FIG. 2) of a conventional arthroscope when the sheath 10 is properly attached to said conventional arthroscope.

The bridge 16 of the conventional scope is similarly slidingly received within cylindrical lock member 18 that is positioned at the proximal end of the novel tool 10. A radially disposed set screw 20 is preferably employed to detachably secure bridge 6 within said lock member 18 as depicted.

A base member 22 having a hollow interior 24 is positioned adjacent the proximal end of tube 12 in open communication with the hollow interior thereof; the opening where said hollow interiors meet is denoted 26 and is referred to as the first opening in the claims that follow.

Figure 3:
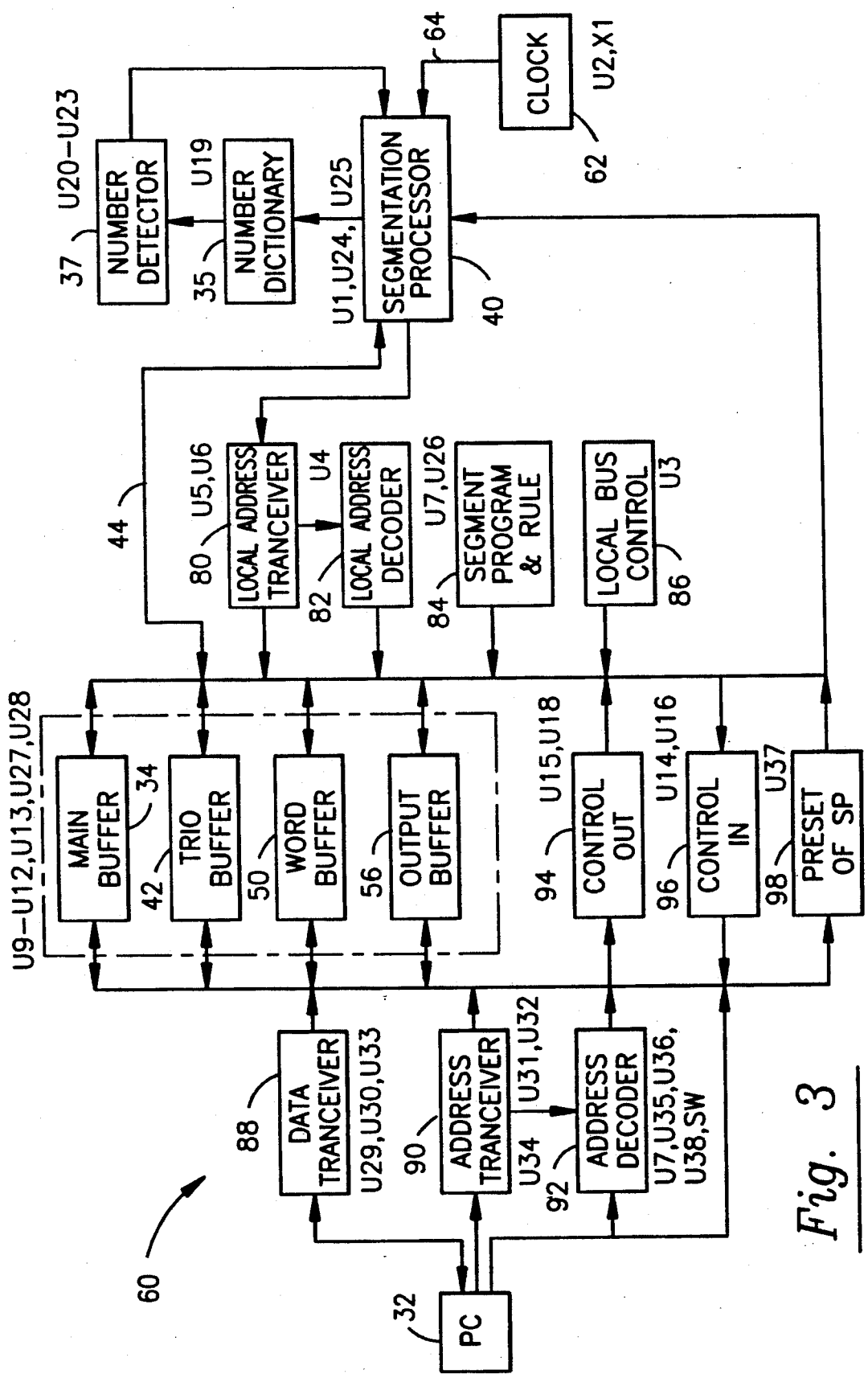
FIG. 3 is a transverse sectional view taken along line 3—3 in FIG. 2.

An irrigation control valve 28 having inlet 27 and outlet or irrigation port 29 is mounted at a perimeter of hollow base 22. An elongate, flexible needle 30 extends from the irrigation port 29 of said valve 28 to the distal end of tube 12; needle 38 has a gradual ninety degree bend formed therein as it passes through opening 26, and it abuts tube 12 along its extent as shown in FIGS. 2 and 3 so as not to obstruct the insertion of the scope's outer casing 14. Manipulation of handle 32 controls the flow rate of irrigating fluid to said site. The external source of irrigation fluid under positive pressure to which the inlet means 27 of valve 28 is connected is not shown.

Suction control valve 34 is of similar construction and is similarly mounted to base 22; it also includes a handle 36 which is under the control of the physician so that the process of vacuuming the irrigation fluid and surgical debris from the site of the surgical procedure can be adjusted as needed.

Irrigation fluid under suction enters the open distal end 11 of tube 2 and passes through opening 26 to enter the hollow interior 24 of base 22. It then enters suction port 38 of valve 34 as indicated by directional arrow 40 and travels to a collection means under negative pressure; the source of the negative pressure is not shown. Suction port 38 is the inlet means for valve 34; the outlet means is denoted 39.

Coherent light is supplied to the site of the surgical procedure through laser tube 50. It is positioned at an acute angle as shown and intercepts tube 12 at opening 52. Opening 52 is referred to as the second opening in the claims. Laser fibers 56 (FIG. 3) are housed within tube 50 and pass through said opening 52. The proximal ends of the laser fibers are connected to an external source of coherent light, not shown, and the distal ends thereof extend to the distal end 11 of the novel sheath 10, external to outer casing 14. Like needle 30, the laser fibers abut the inner cylindrical sidewalls of sheath tube 12 so as not to interfere with insertion of the outer casing 14, as clearly shown in FIG. 3. As indicated in FIGS. 2 and 3, the laser fibers are positioned within sheath tube 12 substantially diametrically opposed to needle 30. Rubber boot 54 is positioned at the proximal end of laser tube 50 when the laser fibers have been slidingly introduced thereinto by the physician; it holds the fibers against movement. Tissue or other substances are vaporized when subjected to pulses of the coherent light, and the debris thereby created is floated within the saline solution delivered to the site through needle 30. The vacuum created by the external source of negative pressure facilitates removal of the irrigation fluid and debris floating therewithin through suction control valve 34.

A physician desiring to make but a single incision and a single insertion of surgical instruments through that single incision simply connects a conventional arthroscope to the novel lumbar arthroscopic laser sheath 10 in the manner set forth above, and connects the irrigation and suction control valves 28 and 34 to their respective sources of positive and negative pressure. Laser fibers are slidingly introduced through the laser tube 50 and said fibers are connected to an external source of coherent light. The surgical procedure can then be performed with a single incision and a single insertion of sheath 10 through that incision.

This invention is clearly new and useful. Moreover, it was not obvious to those of ordinary skill in this art at the time it was made, in view of the prior art when considered as a whole in accordance with the requirements of law.

Moreover, this invention pioneers the art of retrofitable tools for converting single or dual function arthroscopes to multiple function arthroscopes. Accordingly, the claims that follow are entitled to broad interpretation, as a matter of law, so that the heart or essence of this breakthrough invention is protected from piracy.

It will thus be seen that the objects set forth above, and those made apparent from the foregoing description, are efficiently attained and since contain changes may be made in the above construction without departing from the Scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A lumbar arthroscopic sheath, comprising:
   an elongate, hollow, linear-in-configuration tube having a distal end and a proximal end;
   a lock means positioned at said proximal end of said hollow tube;
   said lock means including a cylindrical lock member for slideably receiving a complementary formed part of an arthroscope;
   said lock means further including a radially disposed set screw that screw threadedly engages said cylindrical lock member and that, when advanced, engages said complementary formed part of said arthroscope and holds it within said cylindrical lock member;
   a first opening formed in said hollow tube near said proximal end;
   a hollow, disc-shaped base member mounted about said hollow tube in communication with said first opening so that the hollow interior of said hollow tube and the hollow interior of said base member are in open fluid communication with one another;
   an irrigation control valve mounted to said base member;
   said irrigation control valve having an irrigation port positioned within the hollow interior of said base member and having an inlet means positioned external to said hollow interior of said base member, said inlet means being in fluid communication with a source of irrigation fluid under positive pressure;
   an elongate flexible needle having a proximal end secured to said irrigation port and a distal end substantially contiguous with the distal end of said linear-in-configuration tube;
   said elongate flexible needle extending through said first opening formed in said hollow tube and having a ninety degree bend formed therein where it extends through said first opening;
   a suction control valve mounted to said base member in diametrically opposed relation to said irrigation control valve;
   said suction control valve having a suction port positioned within the hollow interior of said base member and having an inlet means positioned external to said hollow interior, said inlet means being in fluid communication with a source of negative pressure;
   a second opening being formed in said hollow tube, said second opening being formed distally of said first opening and proximal to a free end of said hollow tube; and
   a laser tube having a proximal end and a distal end, said laser tube distal end being disposed in open communication with the hollow interior of said linear-in-configuration hollow tube at said second opening and said laser tube proximal end for connection to a source of coherent light external to said sheath.

2. The sheath of claim 1, wherein said laser tube is disposed at a preselected acute angle with respect to said linear-in-configuration hollow tube.

3. The sheath of claim 2, wherein said laser tube extends through said disk-shaped base member in impaling relation thereto.

* * * * *

UNITED STATES PATENT AND TRADEMARK OFFICE
CERTIFICATE OF CORRECTION

PATENT NO. : 5,203,781　　　　　　　　　　　　Page 1 of 4
DATED　　　 : April 20, 1993
INVENTOR(S) : Alfred O. Bonati, et al.

It is certified that error appears in the above-indentified patent and that said Letters Patent is hereby corrected as shown below:

Title page should be deleted to appear as per attached title page.

Drawing sheets should be deleted to appear as per attached drawing sheets consisting of 3 figures.

Signed and Sealed this

Nineteenth Day of October, 1993

Attest:

BRUCE LEHMAN

Attesting Officer　　　Commissioner of Patents and Trademarks

United States Patent [19]

Bonati et al.

[11] Patent Number: 5,203,781
[45] Date of Patent: Apr. 20, 1993

[54] LUMBAR ARTHROSCOPIC LASER SHEATH

[75] Inventors: Alfred O. Bonati, New Port Richey; Philip Ware, Spring Hill, both of Fla.

[73] Assignee: Meditron Devices, Inc., Hackensack, N.J.

[21] Appl. No.: 814,185

[22] Filed: Dec. 19, 1991

[51] Int. Cl.$^5$ .............................................. A61B 17/36
[52] U.S. Cl. ........................................ 606/15; 606/16; 606/13; 128/4; 128/6
[58] Field of Search ...................... 606/13–16; 128/4, 6, 395, 398

[56] References Cited

U.S. PATENT DOCUMENTS

| | | | |
|---|---|---|---|
| 4,211,229 | 7/1980 | Wurster | 606/14 |
| 4,313,431 | 2/1982 | Frank | 606/16 X |
| 4,597,380 | 7/1986 | Raif et al. | 606/14 X |
| 4,760,840 | 8/1988 | Fournier, Jr. et al. | 606/15 |
| 4,920,961 | 5/1990 | Grossi et al. | 606/14 |
| 4,955,882 | 9/1990 | Hakky | 606/16 X |

Primary Examiner—Stephen C. Pellegrino
Assistant Examiner—Jeffrey A. Schmidt
Attorney, Agent, or Firm—Joseph C. Mason, Jr.; Ronald E. Smith

[57] ABSTRACT

A tool that is retrofit to a conventional arthroscope to add multiple functions. The tool includes a sheath that receives the elongate tube of the arthroscope, and a lock that detachably secures the tool to the arthroscope. A hollow base member is mounted to the sheath, and a first opening formed in the sheath provides fluid communication between the hollow interior of the base member and the sheath. An irrigation control valve is mounted to the base member and supplies irrigation fluid to the site of the surgical procedure through an elongate flexible needle that extends from the irrigation control valve to the distal end of the sheath. A suction control valve has an inlet in communication with a source of negative pressure and vacuums irrigation fluid and surgical debris from the site. A laser tube intersects the sheath at a second opening at an angle and delivers coherent light to the site. Thus, the tool adds a total of three functions to the arthroscope.

3 Claims, 3 Drawing Sheets

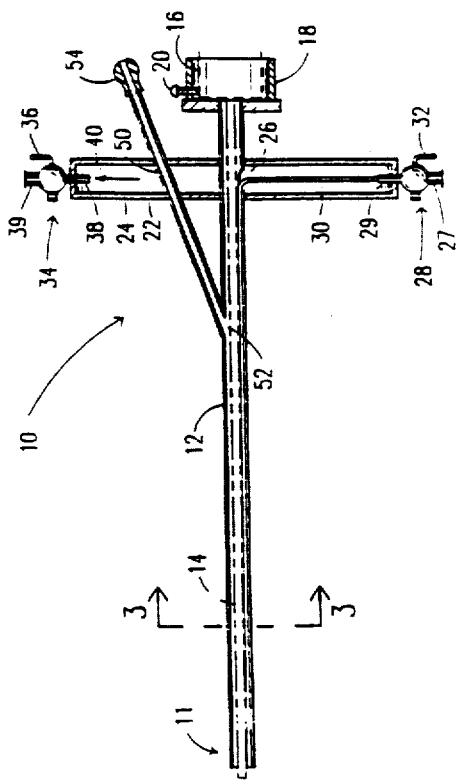

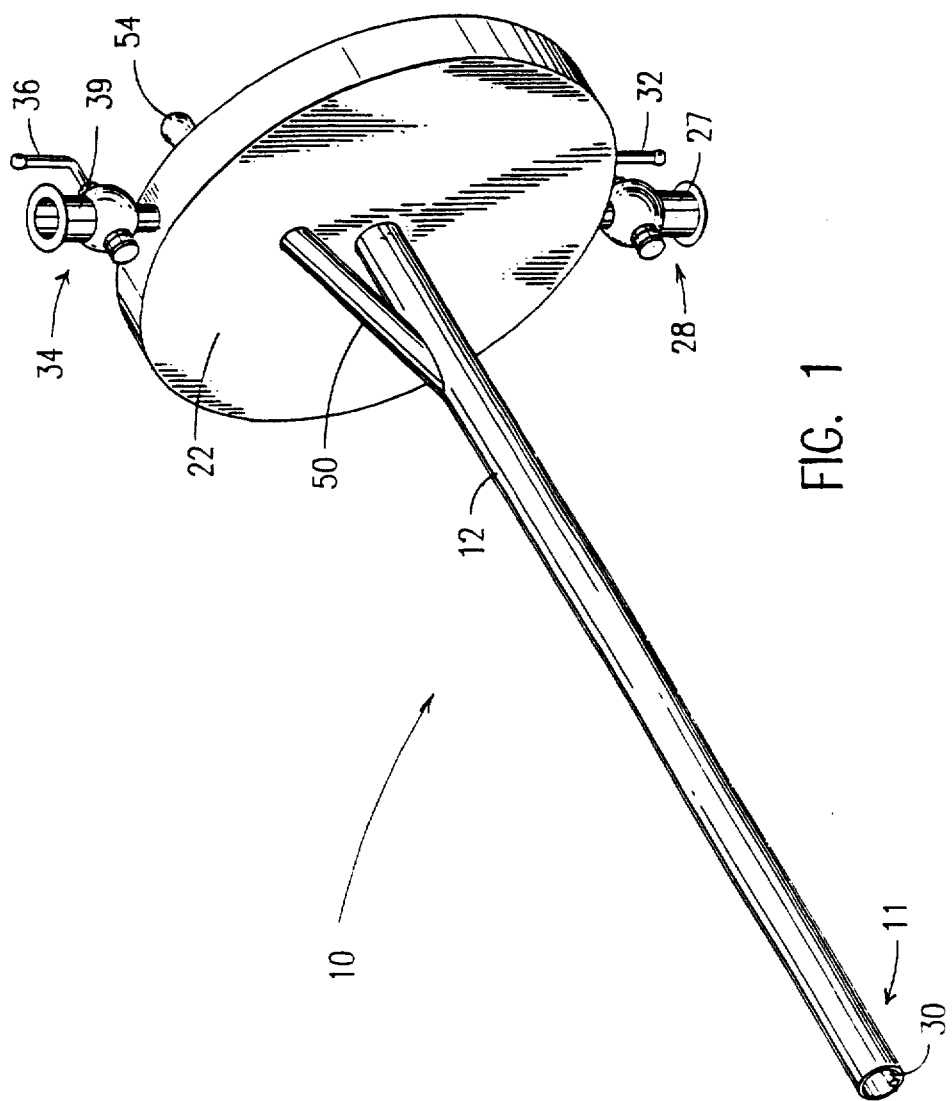

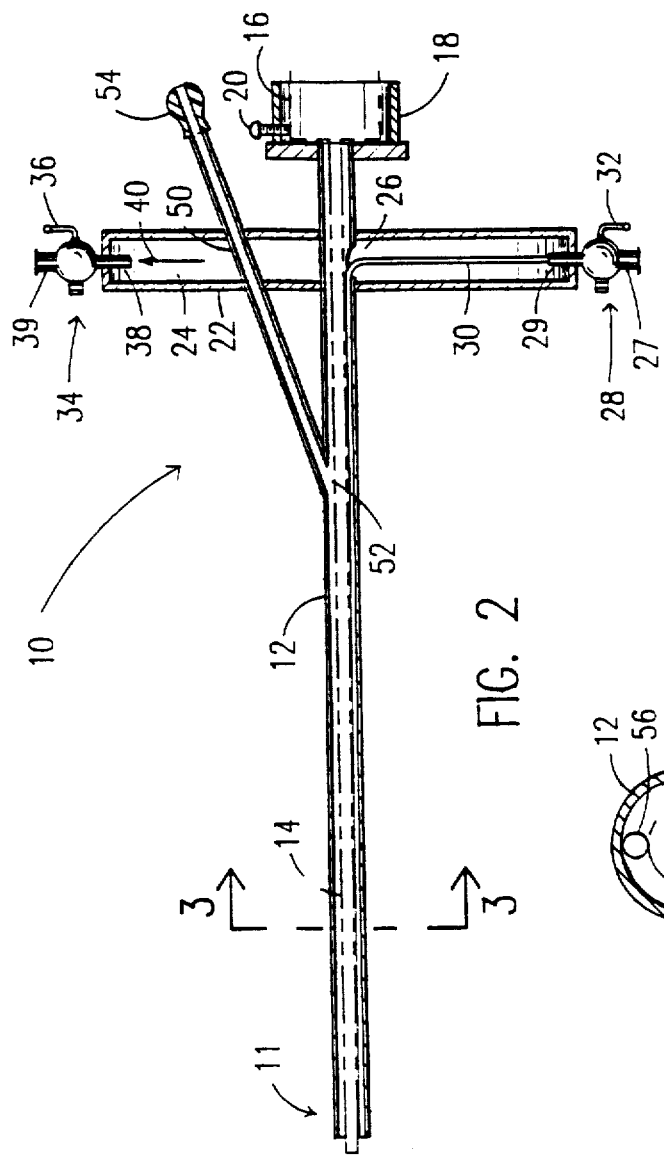
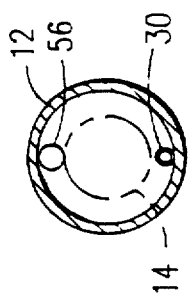
FIG. 2
FIG. 3